United States Patent
Ovadia

(10) Patent No.: US 7,327,447 B2
(45) Date of Patent: *Feb. 5, 2008

(54) INSPECTION SYSTEM FOR LIMITED ACCESS SPACES

(75) Inventor: Yuval Ovadia, Yagur (IL)

(73) Assignee: S.T.I. Security Technology Integration Ltd., Shefayim (IL)

( * ) Notice: Subject to any disclaimer, the term of this patent is extended or adjusted under 35 U.S.C. 154(b) by 83 days.

This patent is subject to a terminal disclaimer.

(21) Appl. No.: 10/528,770

(22) PCT Filed: Sep. 18, 2003

(86) PCT No.: PCT/IL03/00754

§ 371 (c)(1),
(2), (4) Date: Mar. 22, 2005

(87) PCT Pub. No.: WO2004/027373

PCT Pub. Date: Apr. 1, 2004

(65) Prior Publication Data

US 2005/0271184 A1    Dec. 8, 2005

(51) Int. Cl.
*G01N 21/00* (2006.01)
(52) U.S. Cl. .............. 356/237.1; 356/318; 356/73; 378/88
(58) Field of Classification Search .. 356/237.1–237.5, 356/394, 601–623, 432–440, 445, 318, 73; 378/88

See application file for complete search history.

(56) References Cited

U.S. PATENT DOCUMENTS

| | | | |
|---|---|---|---|
| 3,873,837 A | 3/1975 | Palermo, Jr. | |
| 4,585,350 A * | 4/1986 | Pryor | 356/625 |
| 4,652,758 A | 3/1987 | Barfod | |
| 4,989,981 A | 2/1991 | Kawamura et al. | |
| 5,274,549 A | 12/1993 | Almasi | |
| 5,295,073 A | 3/1994 | Celette | |
| 5,376,796 A | 12/1994 | Chan et al. | |
| 5,379,103 A * | 1/1995 | Zigler | 356/73 |
| 5,394,654 A | 3/1995 | Shimbara et al. | |
| 5,477,371 A | 12/1995 | Shafir | |
| 5,521,707 A * | 5/1996 | Castore et al. | 356/394 |
| 5,625,197 A | 4/1997 | Shimbara | |
| 5,671,055 A | 9/1997 | Whittlesey et al. | |
| 5,841,546 A * | 11/1998 | Carangelo et al. | 356/445 |
| 6,147,752 A | 11/2000 | Hewitt et al. | |
| 6,249,567 B1 | 6/2001 | Rothschild et al. | |
| 6,320,654 B1 | 11/2001 | Alders et al. | |
| 6,407,818 B1 | 6/2002 | Whitehouse | |
| 6,417,919 B1 | 7/2002 | Hewitt et al. | |

(Continued)

FOREIGN PATENT DOCUMENTS

| | | |
|---|---|---|
| GB | 2258321 | 3/1993 |
| JP | 404001506 | 7/1992 |
| JP | 11313311 | 9/1999 |

*Primary Examiner*—Hoa Q. Pham

(57) ABSTRACT

A limited access space inspection system comprising: a sensing device for carrying out sensing over a region in the limited access space, a mounting for mounting the sensing device to scan about the limited access space and a scanning control unit, associated with the sensing device, for controlling the sensing device to scan about the limited access space. The device is particularly useful for improving by automation, security checks, customs checks and safety checks involving such awkward to access spaces. The sensing device may be an imaging device, or a sensor for detecting traces of chemical substances.

35 Claims, 8 Drawing Sheets

U.S. PATENT DOCUMENTS

| | | |
|---|---|---|
| 6,600,168 B1 | 7/2003 | Geng |
| 2004/0057042 A1 | 3/2004 | Ovadia |
| 2004/0165750 A1 | 8/2004 | Chew |
| 2005/0200843 A1* | 9/2005 | Kumar et al. ............... 356/318 |

* cited by examiner

INSPECTION SYSTEM FOR LIMITED ACCESS SPACES

RELATED PATENT APPLICATION

This application is a National Phase Application of PCT/1L03/00754 having International Filing Date of 18 Sep. 2003, which claims priority from U.S. patent application Ser. No. 10/252,040 filed 23 Sep. 2002.

FIELD AND BACKGROUND OF THE INVENTION

The present invention relates to an inspection system for limited access spaces and, more particularly, but not exclusively to a vehicle inspection system suitable for inspection of parts of vehicles that are awkward to inspect easily.

Vehicle underside inspection is necessary for several reasons, one being to provide security, a second being for safety and a third being for contraband detection, by customs inspectors and the like. On the security side, undersides of vehicles may have concealed explosive devices. Of particular concern is the possibility of concealing an explosive device on the underside of a fuel tanker, which device is timed or controlled to explode when the tanker is inside a fuel distribution depot. Carrying out detailed manual inspections of the undersides of each tanker entering a fuel depot is both time and labor consuming. On the safety side, the underside of the vehicle may conceal a mechanical flaw, the early detection of which may prevent an accident. In a garage or workshop a car is generally jacked up or placed on a ramp. Larger vehicles are placed on ramps or are driven over inspection pits. However, outside the garage environment, inspection of the underside of a vehicle is difficult. Contraband detection at borders by customs officials is often based on spot checks since customs very rarely have the resources to inspect every passing vehicle. Any means of allowing a more detailed inspection in a smaller time frame would be welcome.

Security checks for entry into government buildings and the like are typically carried out using a mirror on the end of a pole, which is inserted under the vehicle. However, without illumination it is difficult to see much detail and even with illumination, an explosive device can be concealed in a spot that is awkward to view using the mirror. Furthermore such a mirror is very unlikely to spot hairline cracks, which are usually the first signs of dangerous mechanical faults. It is impractical to install inspection pits at all places where regular vehicle checks are desirable.

U.S. Pat. No. 6,249,567 to Rothschild et al discloses an inspection system for inspecting a vehicle moving at a grade of travel over a surface and for detecting material disposed within or on the underside of the vehicle. The system has a source for providing a generally upward or downward pointing beam of penetrating radiation of specified cross-section so as to illuminate vehicles driven above or below the source of radiation. A detector arrangement, disposed below the grade of travel, detects radiation from the beam scattered by any material disposed on the underside of the moving vehicle and generates a scattered radiation signal that may be used for characterizing the material disposed on the underside of the vehicle. Similarly, a detector arrangement disposed above the vehicle generates a scattered radiation signal that may be used for characterizing the material disposed within the vehicle. The system however sits at a single location, requiring the vehicle to move during inspection. It cannot independently scan the vehicle underside. Furthermore, the main detection function of the system is based on x-rays, since a principle intention is to scan for the internal contents of the vehicle.

There is thus a widely recognized need for, and it would be highly advantageous to have, a vehicle inspection system devoid of the above limitations.

SUMMARY OF THE INVENTION

According to one aspect of the present invention there is provided a limited access space inspection system comprising:

a sensing device for sensing within a region in the limited access space, a mounting for mounting the sensing device to be scannable about the limited access space and a scanning control unit, associated with the sensing device, for controlling the sensing device to scan about the limited access space.

The sensing device may be an imaging device or a trace sensing device such as a sniffing device or spectroscopy-based device.

The system preferably comprises a protective housing for protecting the imaging device from the environment by interposing between at least the imaging device and the region to be imaged.

Preferably, the protective housing comprises a transparent region located between the imaging device and the region to be imaged.

Preferably, the transparent region comprises laminated glass.

Preferably, the laminated glass is triplex laminated glass.

Preferably, the mounting is a floor mounting for mounting the imaging device at floor level.

Preferably, the mounting comprises a camera track for movably bearing the imaging device.

Preferably, the mounting comprises guide tracks for guiding a vehicle thereover, an underside of the vehicle thereby forming the limited access space.

Preferably, the mounting is a flush floor mounting for insertion into a floor cavity.

The system preferably comprises an illumination source for providing illumination to the limited access space.

The system preferably comprises a display output for providing a display signal.

Preferably, an image processor is located between the imaging device and the display output to process images from the imaging device prior to output.

Preferably, the image processor is operable to compare a current image of the region with a previous image to detect differences therebetween.

Preferably, the imaging device is linearly movable along the camera track, is rotatable about an axis perpendicular to the track, and is further rotatable about an axis parallel to the track.

Preferably, the scanning control unit is controllable by at least one of direct user input and by preprogramming, to scan the imaging device about the limited access space.

In one embodiment the inspection system is mounted on a mobile trailer.

According to a second aspect of the present invention there is provided a vehicle underside inspection system comprising:

a floor mounted track, an imaging device mounted on the floor track to be linearly movable along the floor track, and a display output, associated with the imaging device, for providing a display signal of output of the imaging device.

The system preferably comprises a scanning controller for controlling the imaging device to scan an imaging region over the floor track.

Preferably, the imaging device is rotatable about an axis perpendicular to the floor track, and is further rotatable about an axis parallel to the floor track.

Preferably, the floor mounted track comprises an outer housing and wherein the imaging device is sealed within the outer housing.

According to a third aspect of the present invention there is provided a method of scanning a limited access space, the method comprising:

interpolating a linear track into the space, the linear track having an imaging device movably mounted thereon, and moving the imaging device along the track, thereby to scan the space.

Preferably, the interpolating the linear track into the space comprises locating a vehicle over the track, an underside of the vehicle forming the limited access space.

The method preferably further comprises interpolating an illumination source into the space.

Preferably, the linear track is flush with a floor.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps such as scanning manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
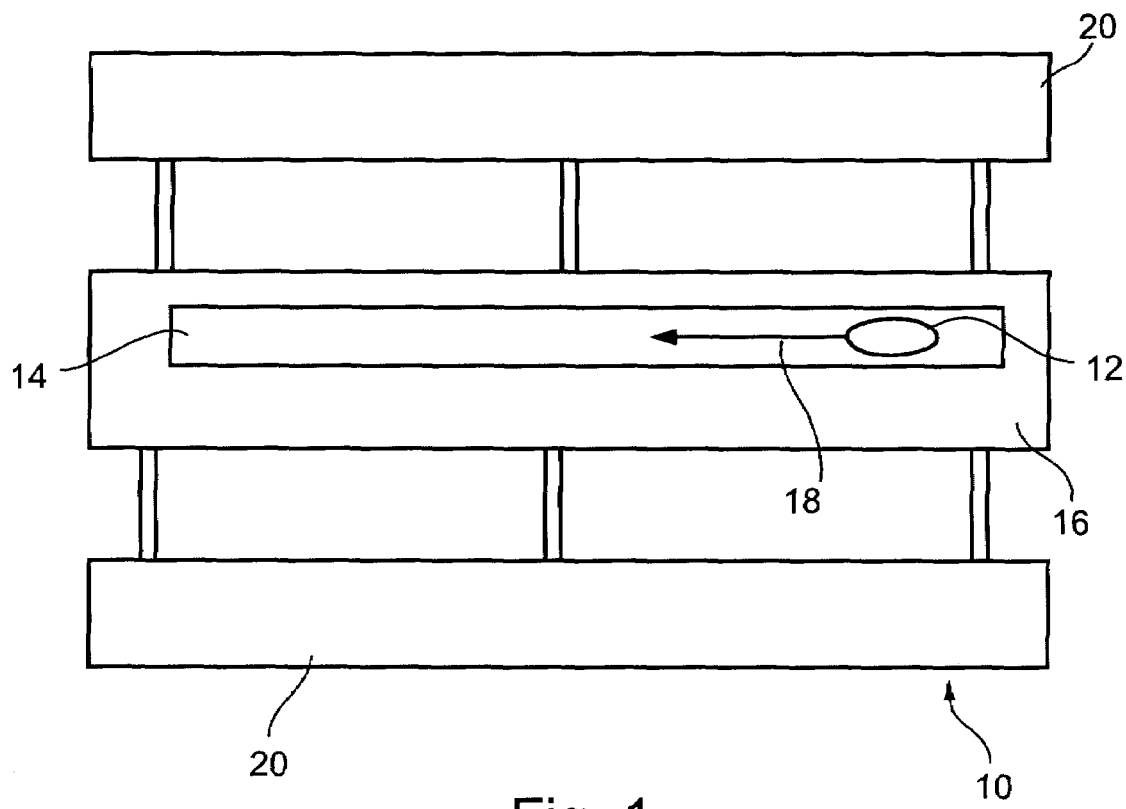
FIG. 1 is a simplified diagram showing a vehicle underside inspection system according to a first preferred embodiment of the present invention.

The present embodiments comprise a controllably movable imaging device mounted on a camera track. The track may be floor mounted to allow vehicles to be driven over it and may further include an illumination source. The floor mounting may for example be part of an inspection pit, or part of a ramp or part of a mobile inspection assembly, as will be described herein. The imaging device, preferably a still or video camera, may be scanned along a vehicle underside as an operator views the resulting images on a screen. The imaging device is preferably sealed under laminated glass to protect from environmental hazards. The camera track may be mounted between vehicle guide tracks.

The principles and operation of a controllably movable imaging device mounted on a camera track according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 illustrates a limited access space inspection system. The inspection system 10 comprises an imaging device 12 for imaging a region in the limited access space. The imaging device 12 is mounted on a track 14 within a track mounting 16. The imaging device 12 is linearly movable along the track 14 in the direction of arrow 18 and is preferably also able to rotate about the track and about an axis perpendicular to the track, the latter at 360°, with the help of controllable actuators. In a preferred embodiment the imaging device is a dome-mounted camera system, such as the Sivis Mini Dome System 3 marketed by Siemens GmbH of Munich, Germany. Such a dome system automatically provides numerous camera movement features such as rotation, tilt, pan, zoom-in, zoom-out and the like and is fully programmable.

The camera is preferably a standard black and white or color still or video camera. In a preferred embodiment the camera is able to alternate between black and white and color modes. Alternatively, depending on what the system is being used to monitor, infra-red, ultra-violet or x-ray or other radiation detectors may be used. For specialized applications such as field use by the military, the camera may be any kind of night vision camera, such as an infra-red camera or an active or passive device based on an image intensifier. Spectrometers and other spectral imaging devices may also be used. Spectrum-based imaging is useful for identifying substances such as explosives.

As an alternative to image detectors, it is possible to use sensing devices that scan for traces of chemical substance. Such devices include sniffing devices, which are able to detect extremely low concentrations of substance. As well as sniffing devices, laser based spectrometers can be used. An example of a laser based spectrometer that can be used is the portable aerosol beam-focused laser-induced plasma spectrometer described at http://www.epa.gov/ttn/emc/meetnw/harre.pdf, the contents of which are hereby incorporated by reference in their entirety. The device is described in relation to the detection of metals, but is suitable for other substances such as the nitro-type substances likely to be found in explosives. Another suitable device which can be used in conjunction with the present invention, is that disclosed at http://www.hud.ac.uk/schools/applied_sciences/chem/TDL-Group/freibpap.htm, the contents of which are hereby incorporated by reference.

The track mounting 16 is preferably located between vehicle guide tracks 20, to allow a vehicle to position itself above the imaging device 12. The track mounting is preferably designed to be inserted into the floor so that a vehicle simply has to drive onto the vehicle guide tracks to provide the imaging device with a clear view of the underside of the vehicle.

Figure 2:
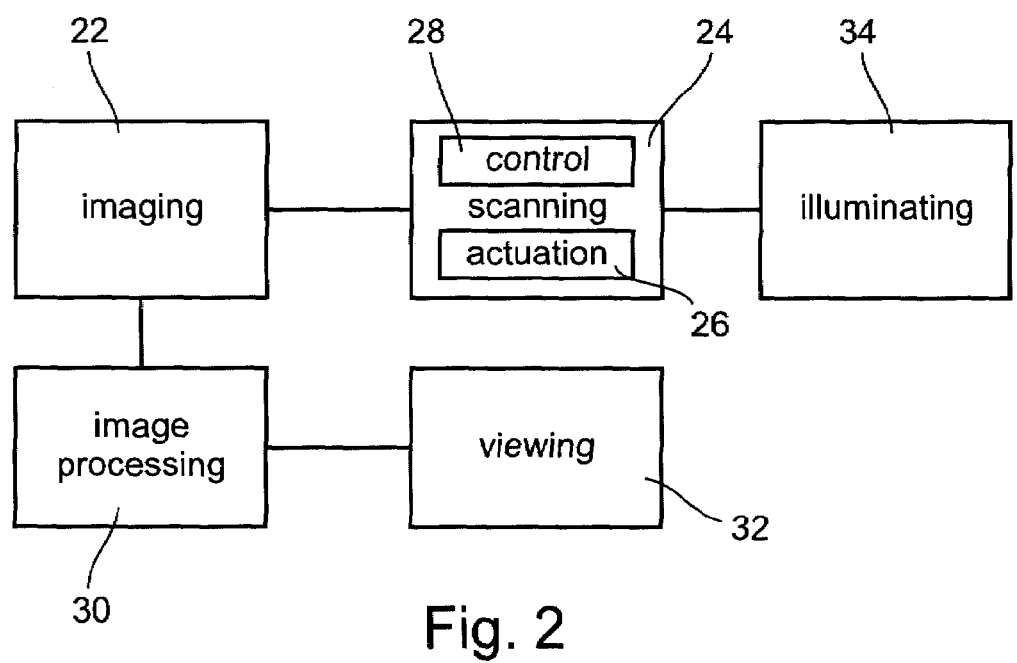
FIG. 2 is a simplified block diagram showing electronic subsystems of the vehicle underside inspection system of FIG. 1.

Reference is now made to FIG. 2, which is a simplified block diagram showing the various electronic subsystems of the inspection system of FIG. 1. An imaging subsystem 22 comprises a camera or other imaging device and associated imaging electronics. A scanning subsystem 24 comprises a scanning control subsystem 26 and an actuation subsystem 28. The actuation subsystem moves the camera through linear and rotary motion in accordance with instructions from the scanning control subsystem. The scanning control subsystem controls the camera to scan the vehicle underside, either according to a pre-recorded program or according to instructions received from the user or operator as he views the output on a screen.

An image processing subsystem 30 carries out various image-processing operations additional to those that a typical camera may normally provide. For example it may increase contrasts, use an overall lighting level to select between color and black and white modes, and in a particularly preferred embodiment may carry out alignment between a current image and a stored image and then carry out a comparison in order to detect differences between the two images. Such a comparison is useful for mechanical inspections of the same vehicle. That is to say an inspection of a given vehicle may be compared with an earlier inspection of the same vehicle so as to detect the appearance of cracks or the development of existing cracks. In automated security comparison may be made with a stored image of the same type of vehicle so as to highlight obvious differences such as the insertion of an explosive device.

A viewing subsystem 32 takes output either directly from the imaging subsystem 22 or from the image processing subsystem 30 and displays it. The viewing subsystem 22 may use any kind of visual display unit. An illumination subsystem 34 preferably comprises a light or other illumination source, which preferably moves along with the imaging device 12. If a radiation detector for radiation other than light is used then the illumination source is selected accordingly.

Figure 3:
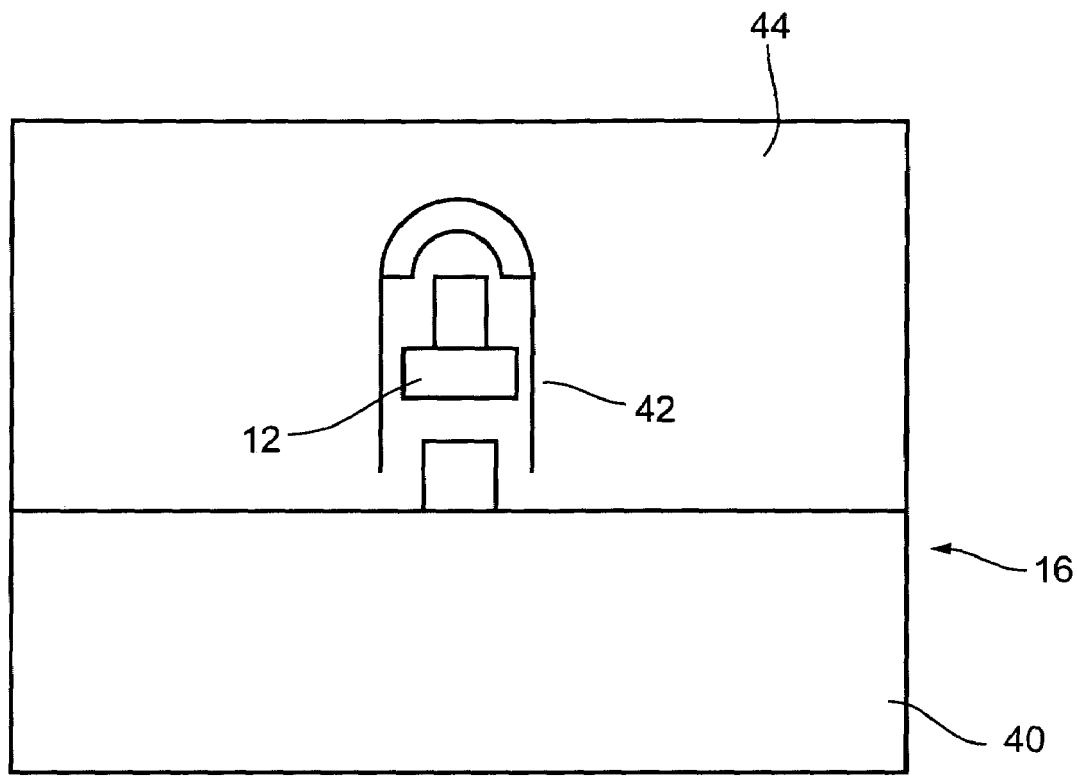
FIG. 3 is a simplified cross section of the vehicle underside inspection system of FIG. 1.

Reference is now made to FIG. 3, which is a simplified cross-section of the track mounting 16 of FIG. 1. Track mounting 16 comprises a base 40 upon which is mounted camera track 14. Camera track 14 may be toothed along its length to improve traction and accuracy of the actuation system. The imaging device 12 is preferably mounted within a dome construction 42, as described above. Track mounting 16 further comprises a protective housing 44 for protecting the imaging device from the environment. The protective housing preferably seals the imaging device and supporting electronics from the external environment. At the very least the protective housing interposes between the imaging device and the region to be imaged, thus protecting the imaging device from oil spillage, knocks and other hazards.

Preferably, the protective housing comprises a transparent region located between the imaging device and the region to be imaged. In an embodiment, the transparent region comprises laminated glass, and in a prototype triplex laminated glass of 22 mm thickness was used.

Preferably, the mounting is a floor mounting for mounting the imaging device at floor level. In a particularly preferred embodiment, the mounting is a flush floor mounting for insertion into a floor cavity.

Figure 4:
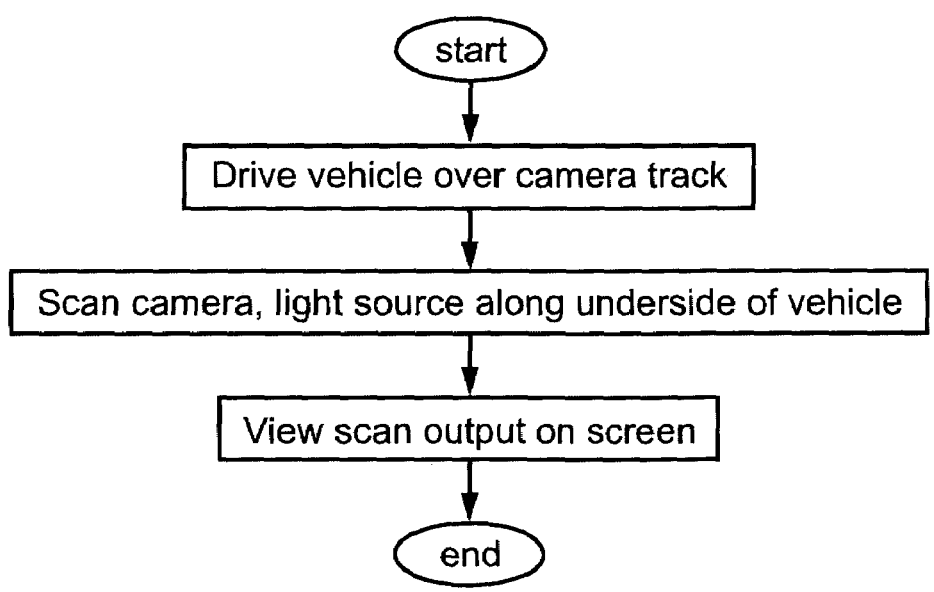
FIG. 4 is a flow chart showing a first embodiment of operation of the system of FIG. 1.

Reference is now made to FIG. 4, which is a simplified flow chart showing operation of a preferred embodiment of the present invention. In FIG. 4 a vehicle is driven onto a rail carrying an imaging device. The invention is not however restricted to "drive-on" inspection of vehicles and thus, as an alternative, it is possible to insert a rail carrying an imaging assembly into any kind of space that it is difficult to access and then to operative the assembly to scan the space. In either case, the imaging device then scans the space, either under control of a program or according to instructions from an operator. The output is viewed and the operator decides whether any kind of action is necessary. The output may additionally be recorded if desired.

Figure 5:
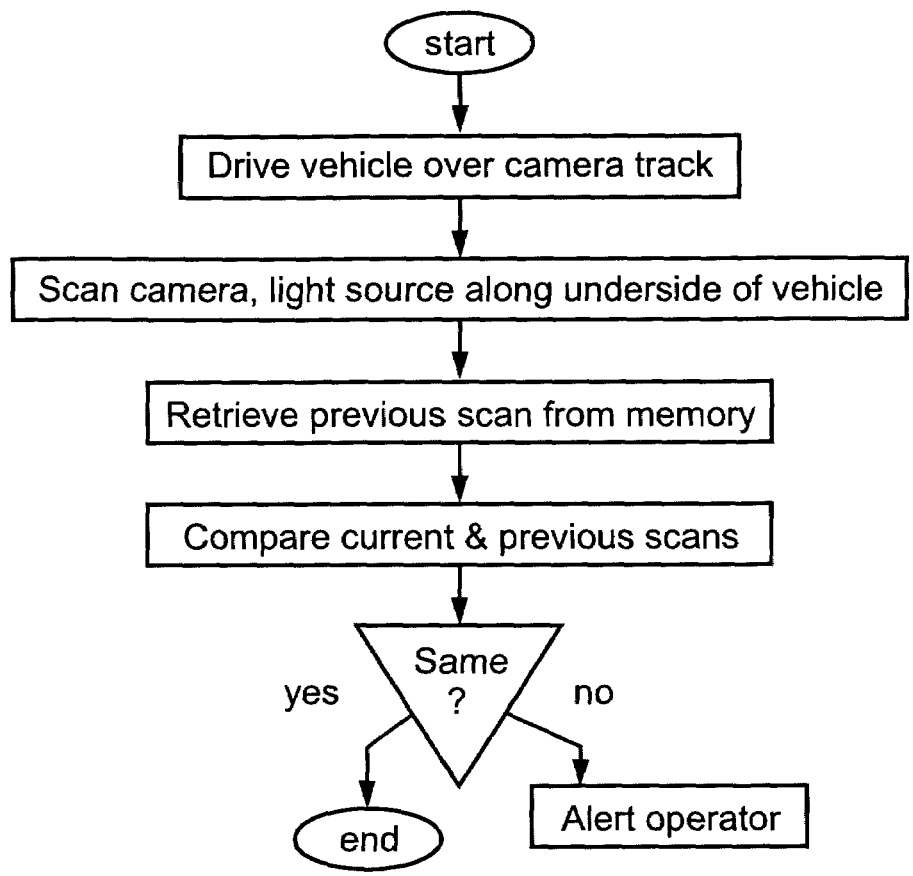
FIG. 5 is a flow chart showing a second embodiment of operation of the system of FIG. 1.

Reference is now made to FIG. 5, which is a flow chart showing operation according to an alternative embodiment of the present invention. Stages that are identical to those of FIG. 4 are not described again except as necessary for an understanding of the present embodiment. In FIG. 5 the positioning and scanning stages are the same. However at that point a previous scan of the same vehicle or same kind of vehicle is retrieved if available and a comparison is carried out between the two scans. The operator is then alerted regarding any differences.

Figure 6:
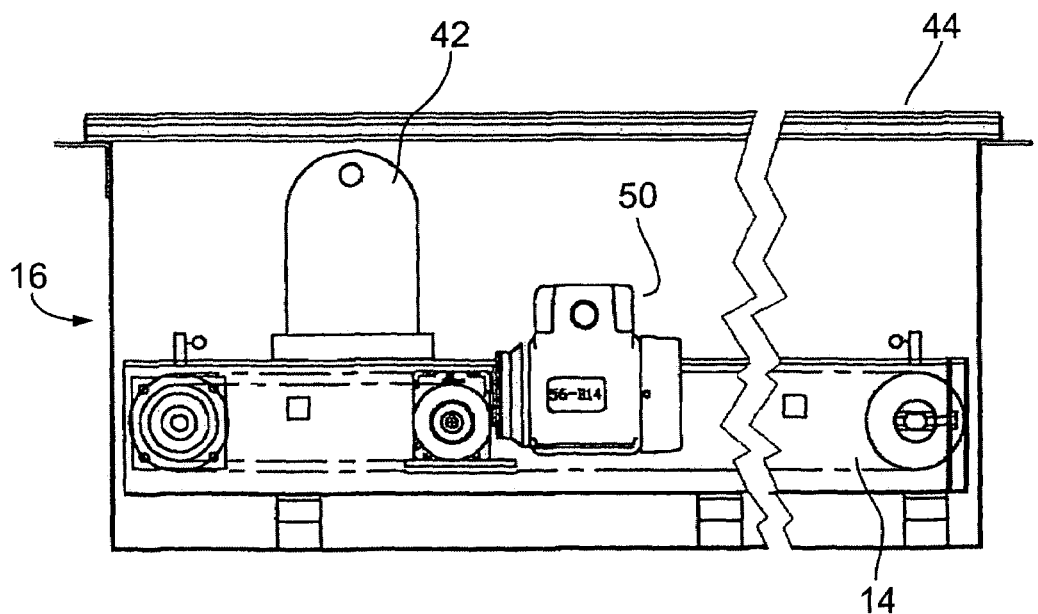
FIG. 6 is a schematic diagram showing assembly details of a prototype embodiment of the present invention viewed from the side.
Figure 7:
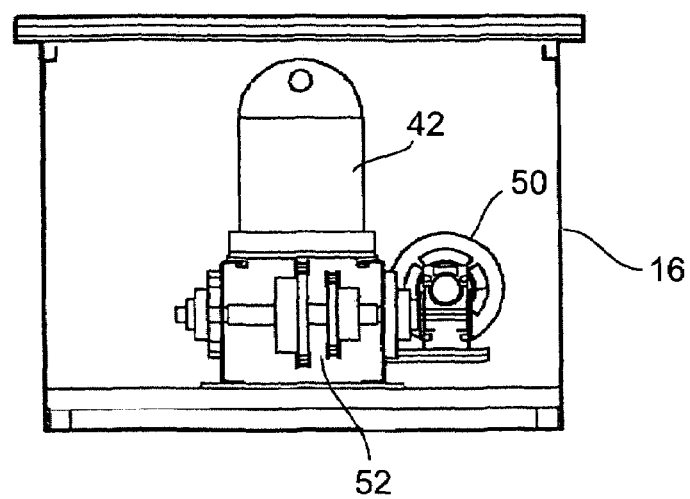
FIG. 7 is a schematic diagram showing assembly details of the same prototype as viewed along the direction of the track.

Reference is now made to FIG. 6, which is a simplified schematic diagram showing assembly details of a prototype embodiment of part of an inspection system according to the present invention viewed from the side. Reference is simultaneously made to FIG. 7 which shows the same assembly viewed along the direction of the rail. Parts that are the same as in previous figures are given the same reference numerals and are not described again except to the extent necessary for an understanding of the present figure. The dome construction 42 is located on track 14 which itself is located on track mounting 16. A motor 50 is provided alongside the dome construction 42 to provide the dome construction with traction to run along the track 14. The motor 50 powers toothed pulleys 52, which intermesh with a toothed central runway of the track 14, thereby to provide the traction.

Figure 8:
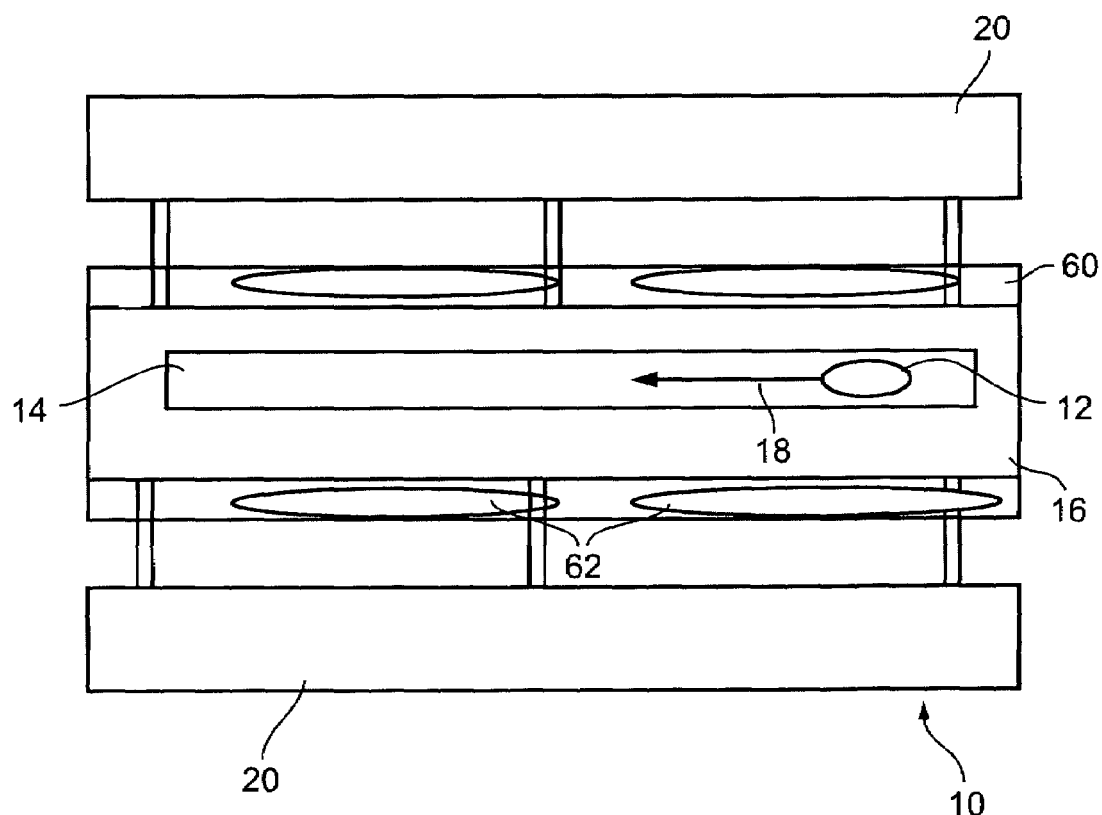
FIG. 8 is a schematic diagram illustrating a further embodiment of the present invention having lighting tracks on either side of the camera track.

Reference is now made to FIG. 8, which is similar to FIG. 1. Parts that are the same as in FIG. 1 are given the same reference numerals and are not referred to again except as necessitated for an understanding of the present embodiment. FIG. 8 differs from FIG. 1 in that it includes a built in lighting track 60 on either side of the camera track 14. The lighting track 60 preferably comprises fluorescent tubes 62.

Figure 9:
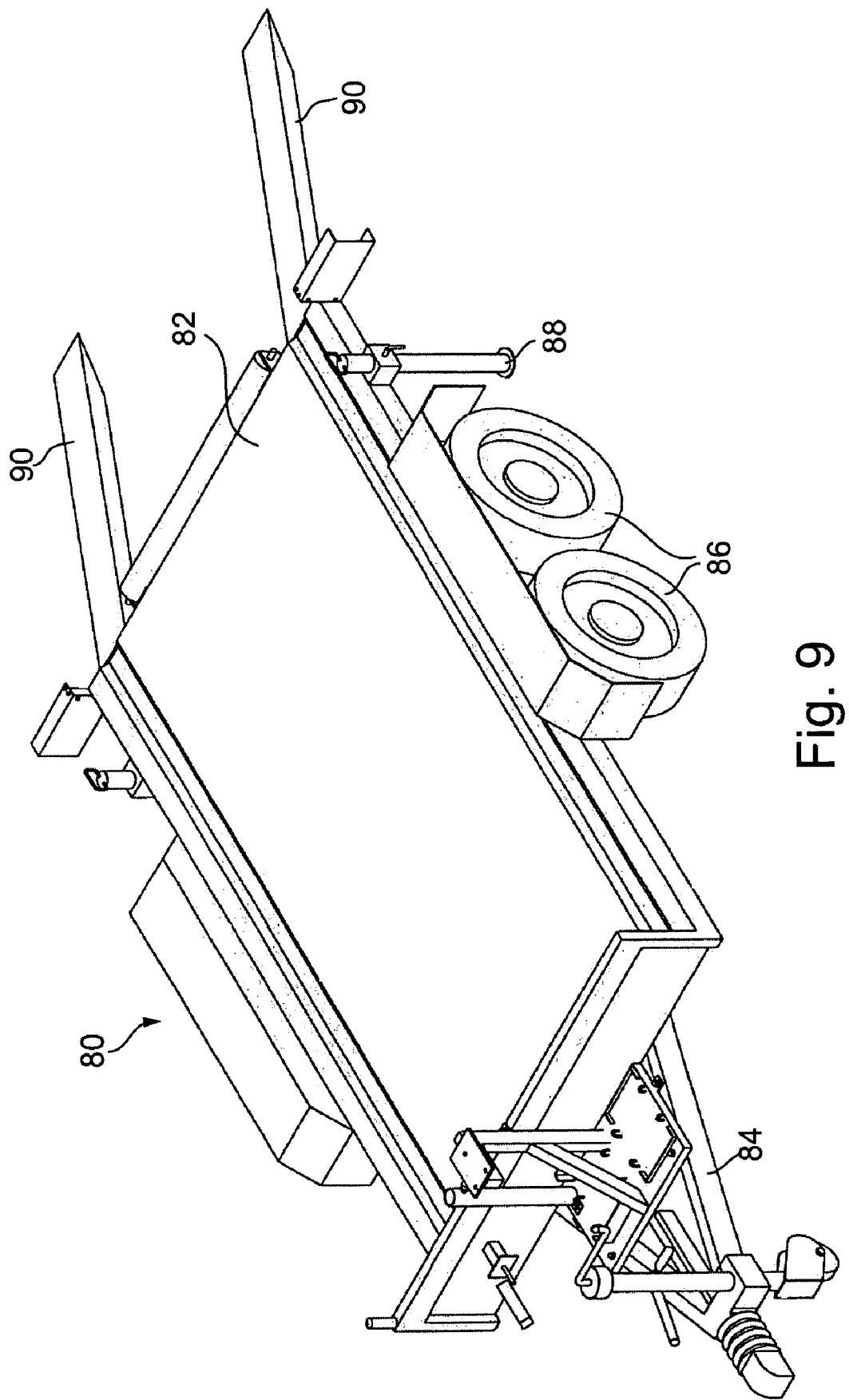
FIG. 9 is a schematic diagram illustrating a mobile trailer for mounting an inspection assembly in order to provide a mobile embodiment of the present invention.

Reference is now made to FIGS. 9-12, which are simplified diagrams showing a further preferred embodiment of the present invention. The embodiment shown in FIGS. 6 and 7 is intended for mounting inside an inspection pit or under a ramp as a permanent fixing. However there is also a need for a mobile version. The mobile version may be used as a demonstrator or it may be used for providing temporary or short term security. FIG. 9 shows a mobile trailer 80 comprising a platform 82, a coupling assembly 84 for attaching to a motorized vehicle for traction, wheels 86 and extendible legs 88. The trailer also has pivotable ramp members 90 to allow an inspection assembly to be raised onto the trailer.

Figure 10:
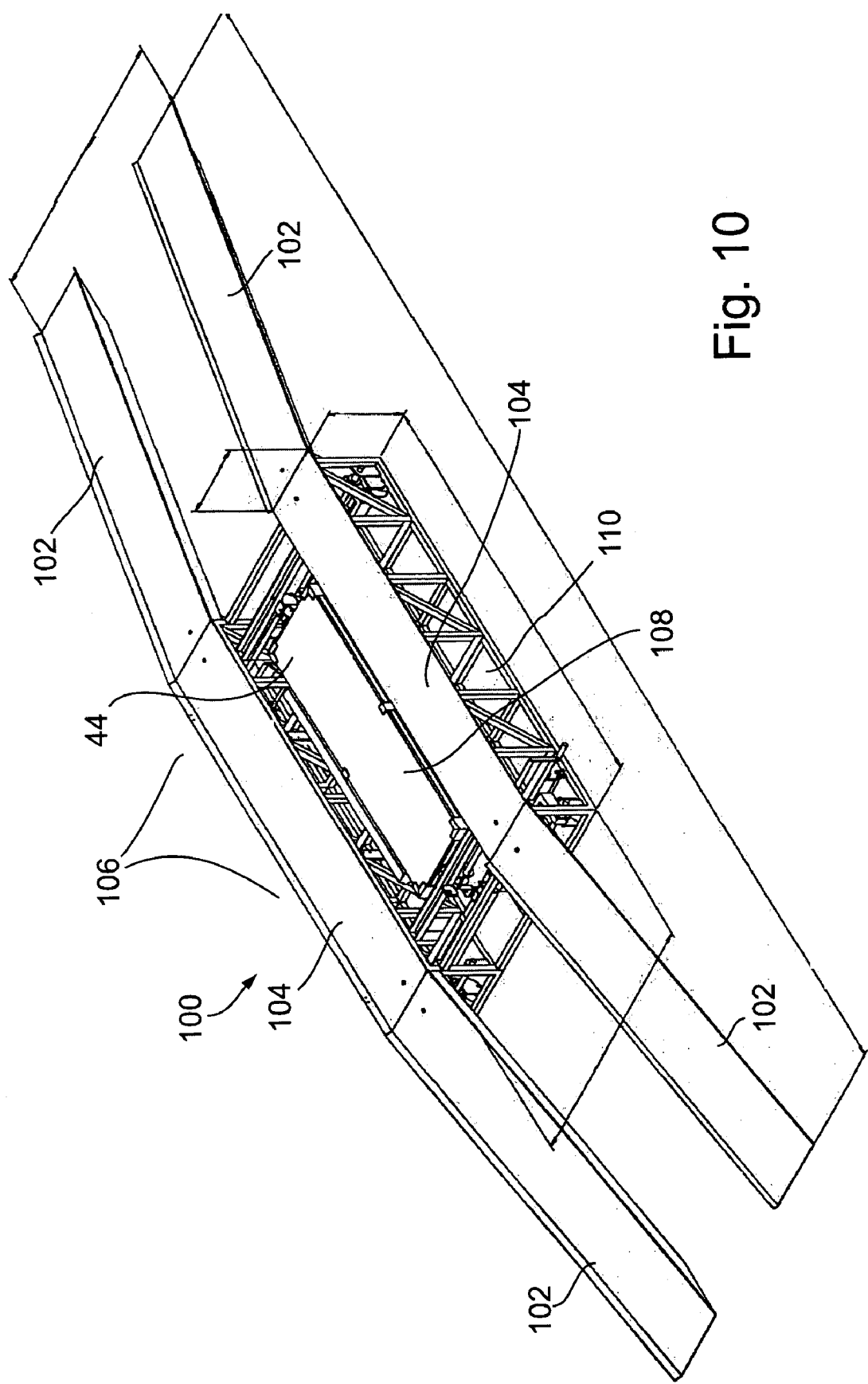
FIG. 10 is a schematic diagram illustrating an inspection assembly for mounting on the trailer of FIG. 9.

FIG. 10 shows an inspection assembly 100 which is suitable for mounting on trailer 80. The inspection assembly 100 comprises pivotable ramp members 102 on either side at front and back. The ramp members are folded for transport and opened out to provide a ramp to allow vehicles to mount the assembly.

Track members 104 link forward and rear ramp members over central section 106 of the assembly. The track members provide a track for a vehicle to pass over and stop over the central section. Between the two track members 104 is an inspection hollow 108 in which the camera and camera track may be mounted within protective housing 44. The content of the inspection hollow is preferably as described in the previous embodiment. The track members 104 are raised on supports 110 so as to provide the vertical space needed for the inspection hollow to be able to accommodate the camera and track.

Figure 11:
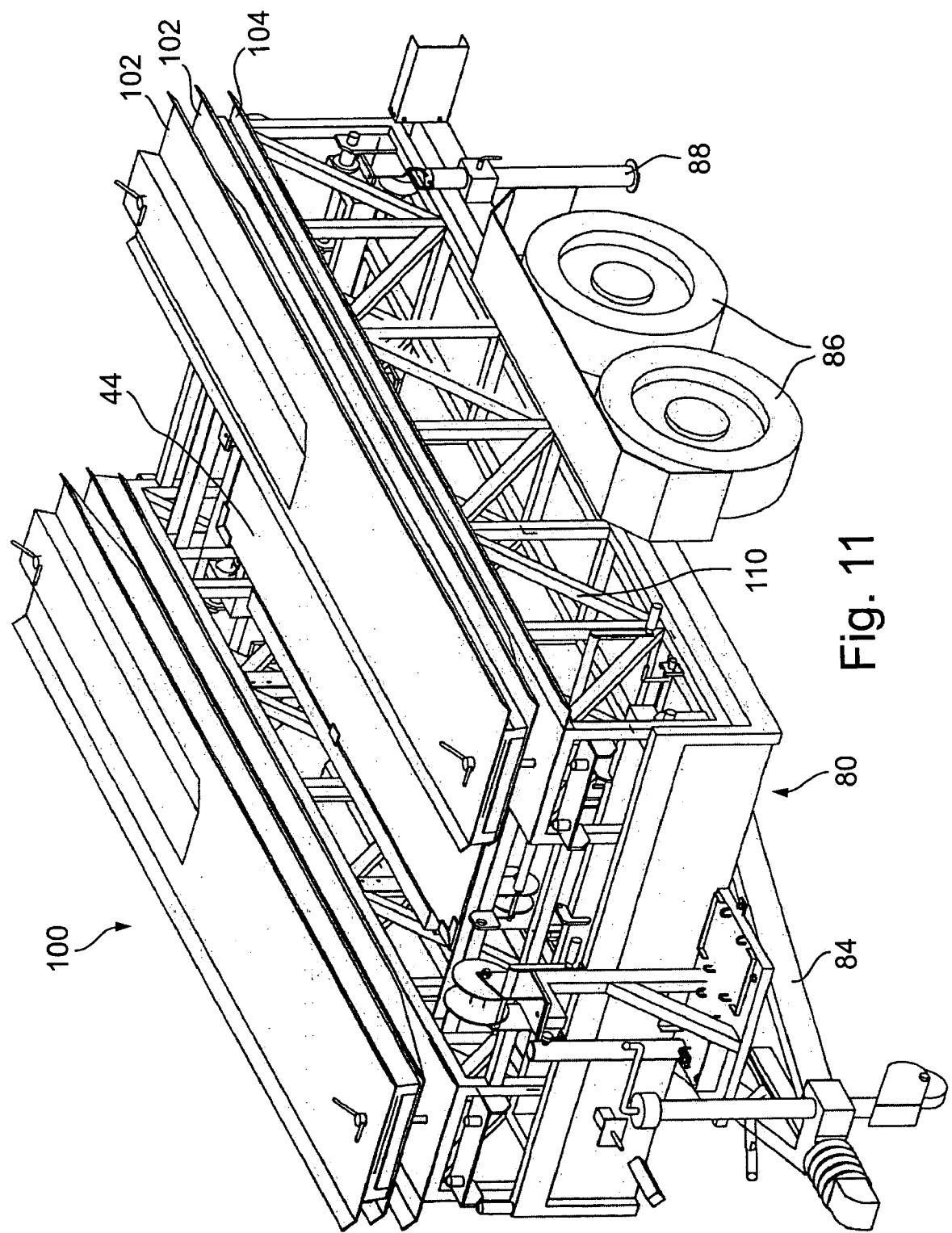
FIG. 11 is a schematic diagram illustrating the inspection assembly of FIG. 10 mounted on the mobile assembly of FIG. 9.

FIG. 11 is a schematic view showing the mobile trailer 80 with the inspection assembly mounted thereon. Parts that are the same as in previous figures are given the same reference numerals and are not described again, except as necessary for an understanding of the present figure. In FIG. 10, the assembly ramp members 102 are shown folded over the track members 104, ready for travel.

Figure 12:
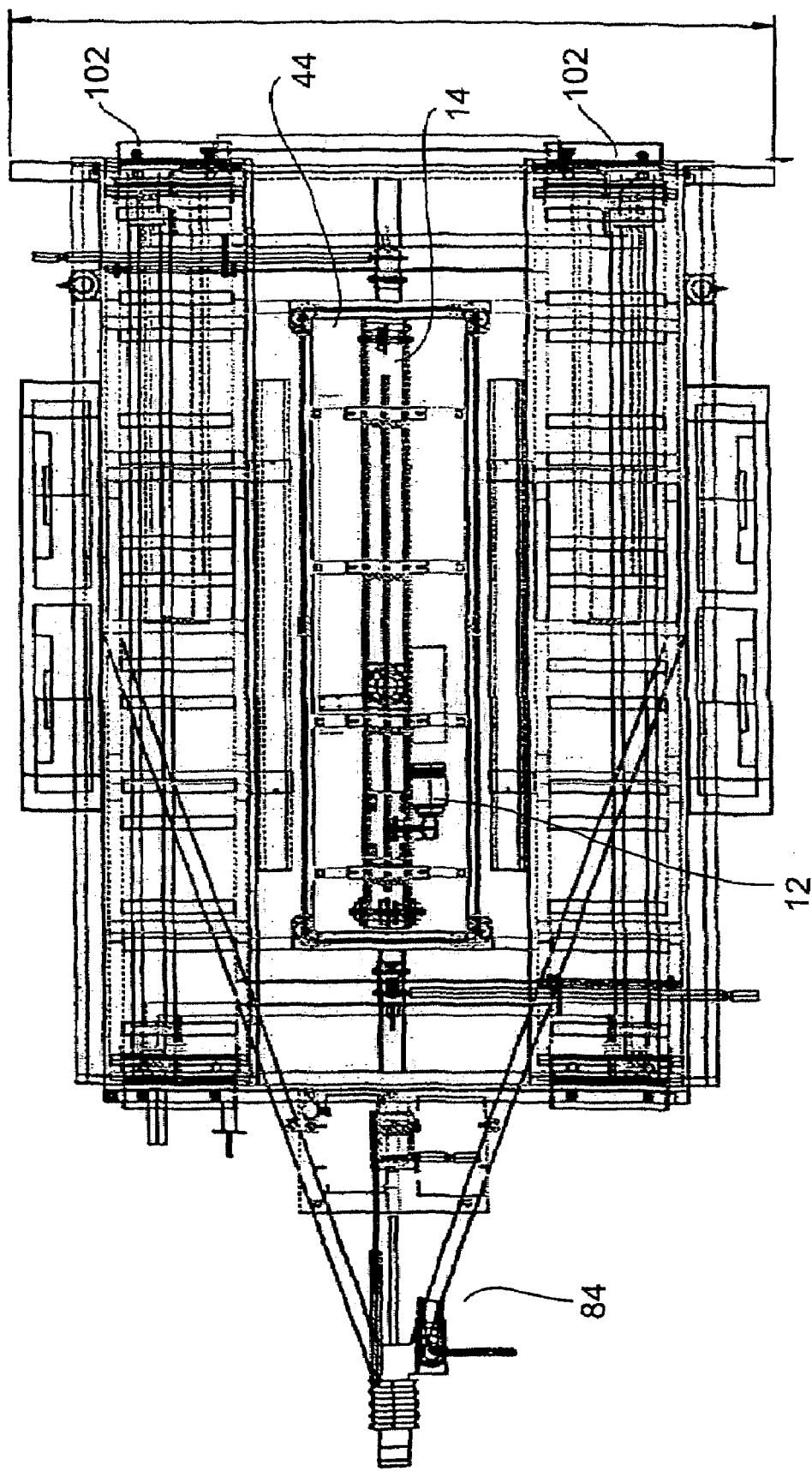
FIG. 12 is a view from above of the assembled mobile inspection assembly.

FIG. 12 is a schematic view from above showing the assembly 100 mounted on trailer 80. Again the ramp members are folded. The camera track 14, and camera mounting 12, are seen in the inspection hollow 108, flanked on either side by lighting tracks 60.

It is expected that during the life of this patent many relevant imaging devices and systems will be developed and the scope of the terms herein, particularly of the terms "camera" and "imaging system", is intended to include all such new technologies a priori.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A limited access space inspection system for inspecting by scanning instances of a predetermined set of defined limited access spaces, the system comprising:
    a sensing device configured for scannably sensing over a region in said limited access space,
    a mounting for mounting said sensing device to be scannable about said limited access space and
    a scanning control unit, associated with said sensing device, for controlling said sensing device to scan about said limited access space according to a prerecorded program, said program selectable for said instance within said set and comprising instructions for moving said sensing device linearly along a track, for rotating said sensing device about an axis perpendicular to said track, and for rotating said sensing device about an axis parallel to said track, thereby to configure said scan for said instance.

2. The system of claim 1, wherein said sensing device is an imaging device.

3. The system of claim 2, wherein said imaging device is any one of a group of devices comprising an optical imaging device, a video camera, an image intensifier, an x-ray imager, a spectrometer, an ultra-violet imager and an infrared imager.

4. The system of claim 2, further comprising a protective housing for protecting said imaging device from the environment by interposing between at least said imaging device and said region to be imaged.

5. The system of claim 2, further comprising an illumination source for providing illumination to said limited access space.

6. The system of claim 2, further comprising an image processor, located between said imaging device and a display output, to process images from said imaging device prior to output for display.

7. The system of claim 6, wherein said image processor is operable to compare a current image of said region with a previous image to detect differences therebetween.

8. The system of claim 1, wherein said sensing device is a trace sensing device for sensing traces of the presence of predefined chemical substances.

9. The system of claim 8, wherein said trace sensing device is a sniffing device for detecting chemical signatures of said predefined substances.

10. The system of claim 8, wherein said trace sensing device is a spectrometer.

11. The system of claim 10, wherein said spectrometer is a laser spectrometer.

12. The system of claim 1, wherein said protective housing comprises a transparent region located between said sensing device and said region to be imaged.

13. The system of claim 12, wherein said transparent region comprises laminated glass.

14. The system of claim 13, wherein said laminated glass is triplex laminated glass.

15. The system of claim 1, wherein said mounting is a floor mounting for mounting said sensing device at floor level.

16. The system of claim 15, wherein said mounting is a flush floor mounting for insertion into a floor cavity.

17. The system of claim 1, wherein said mounting comprises a camera track for movably bearing said sensing device.

18. The system of claim 17, wherein said sensing device is linearly movable along said camera track, is rotatable about an axis perpendicular to said track, and is further rotatable about an axis parallel to said track.

19. The system of claim 18, wherein said scanning control unit is controllable by at least one of direct user input and by preprogramming, to scan said sensing device about said limited access space.

20. The system of claim 1, wherein said mounting comprises guide tracks for guiding a vehicle thereover, an underside of said vehicle thereby forming said limited access space.

21. The system of claim 1, further comprising a display output for providing a display signal.

22. The system of claim 1, wherein said mounting is located on a mobile unit.

23. A vehicle underside inspection system comprising:
a floor mounted track,
a sensing device mounted on said floor track to be linearly movable along said floor track,
a scanning control Unit, associated with said sensing device, configured to control said sensing device to sense about the vehicle underside according to a pre-recorded program, said program being variable between vehicle type, comprising instructions for moving said sensing device linearly along a track, for rotating said sensing device about an axis perpendicular to said track, and for rotating said sensing device about an axis parallel to said track, said program thereby configuring said scan for specific vehicle type, and an output, associated with said sensing device, for providing a display signal of output of said sensing device.

24. The system of claim 23, wherein said sensing device is an imaging device.

25. The system of claim 24, wherein said imaging device is any one of a group comprising an optical imaging device, a video camera, an infra-red imaging device, an ultra-violet imaging device, a spectrometer and an x-ray imaging device.

26. The system of claim 24, further comprising a scanning controller for controlling said imaging device to scan an imaging region over said floor track.

27. The system of claim 26, wherein said imaging device is rotatable about an axis perpendicular to said floor track, and is further rotatable about an axis parallel to said floor track.

28. The system of claim 24, wherein said floor mounted track comprises an outer housing and wherein said imaging device is sealed within said outer housing.

29. The system of claim 24, wherein said floor mounted track is located on a platform of a mobile unit.

30. The system of claim 23, wherein said sensing device is a trace sensing device for detection of traces of a predetermined chemical substance.

31. A method of scanning a limited access space of a set of differently configured spaces, the method comprising:
interpolating a linear track into said space, said linear track having a sensing device movably mounted thereon, recording a scanning program, thereby to provide specific scanning programs for each member of said set, and controlling said sensing device to move according to said recorded scanning program, thereby to scan said space, wherein said recorded scanning program comprises instructions for moving said sensing device linearly along said track, instructions for rotating said sensing device about an axis perpendicular to said track, and instructions for rotating said sensing device about an axis parallel to said track, thereby to provide a scan which is specific to said space.

32. The method of claim 31, wherein said interpolating said linear track into said space comprises locating a vehicle over said track, an underside of said vehicle forming said limited access space.

33. The method of claim 32, wherein said linear track is flush with a floor.

34. The method of claim 31, further comprising interpolating an illumination source into said space.

35. A limited access space inspection system for inspecting members of a set of defined limited access spaces, comprising:
a non-optical sensing device for non-optically sensing over a region in said limited access space,
a mounting for mounting said sensing device to be scannable about said limited access space, and
a scanning control unit, associated with said sensing device, and configured for controlling said sensing device to scan about said limited access space according to a pre-recorded program, said program being adapted for said member and comprising instructions for moving said sensing device linearly along a track, for rotating said sensing device about an axis perpendicular to said track, and for rotating said sensing device about an axis parallel to said track, thereby to provide a scan specific for said member.

* * * * *